(12) United States Patent
Ritt

(10) Patent No.: US 6,528,803 B1
(45) Date of Patent: Mar. 4, 2003

(54) AUTOMATED CALIBRATION ADJUSTMENT FOR FILM DOSIMETRY

(75) Inventor: Daniel M. Ritt, Colorado Springs, CO (US)

(73) Assignee: Radiological Imaging Technology, Inc., Colorado Springs, CO (US)

(*) Notice: Subject to any disclaimer, the term of this patent is extended or adjusted under 35 U.S.C. 154(b) by 0 days.

(21) Appl. No.: 09/489,375

(22) Filed: Jan. 21, 2000

(51) Int. Cl.[7] .................................................. G01T 1/08
(52) U.S. Cl. .............................. 250/473.1; 250/475.2; 250/252.1
(58) Field of Search .......................... 250/473.1, 475.2, 250/472.1, 252.1 A; 378/207

(56) References Cited

U.S. PATENT DOCUMENTS

| | | |
|---|---|---|
| 5,063,583 A | 11/1991 | Galkin |
| 5,276,726 A | 1/1994 | Galkin |
| 5,406,612 A | 4/1995 | Galkin |
| 5,544,238 A | 8/1996 | Galkin |
| 5,844,965 A | 12/1998 | Galkin |

FOREIGN PATENT DOCUMENTS

FR  2678745  1/1993

OTHER PUBLICATIONS

"Radiation Therapy Film Dosimetry System, Version 3.05 For Windows NT 4.0 and Windows '95 User's Manual and Guide," RIT, 01/98.

"Clinical electron–beam dosimetry: Report of AAPM Radiation Therapy Committee Task Group No. 25," Faiz M. Khan, Karen P. Doppke, Kenneth R. Hogstrom, Gerald J. Kutcher, Ravinder Nath, Satish C. Prasad, James A. Purdy, Martin Rozenfeld, and Barry L. Werner, Med. Phys., 18(1), pp. 73–109, Jan./Feb. 1991.

"Film dosimetry of megavoltage photon beams: A practical method of isodensity–to–isodose curve conversion[a]," Med. Phys., 8(1), pp. 94–98, Jan. 1991.

"A new approach to film dosimetry for high energy photon beams: Lateral scatter filtering," Sandra E. Burch, Kimberlee J. Kearfott, Jon H. Trueblood, W. Chris Sheils, J. Inhwan Yeo, C.K. Chris Wang, Med. Phys., 24 (5), pp. 775–783, May 1997.

Primary Examiner—Georgia Epps
Assistant Examiner—Richard Hanig
(74) Attorney, Agent, or Firm—Rader, Fishman & Grauer PLLC (57) ABSTRACT

The present invention provides a method of correcting errors in film dosimetry measurements arising from variations in radiographic film processing and manufacturing. The method includes: (1) irradiating separate and distinct areas of one or more calibration films with different radiation dose levels to obtain a first calibration; (2) exposing a non-irradiated portion of at least one (and typically all) of the calibration films to light from an array of standardized light sources to obtain a first optical density step gradient; (3) exposing a non-irradiated portion of subsequent test films to light from the array of standardized light sources to obtain a second optical density step gradient; and (4) modifying the first calibration or optical density values of the test films based on differences between the first and second optical density step gradients. Since the characteristics of each of the standardized light sources vary little from one exposure to the next, any deviations in the optical density step gradient among different films results, presumably, from changes in film processing or differences in film chemistry.

14 Claims, 7 Drawing Sheets

AUTOMATED CALIBRATION ADJUSTMENT FOR FILM DOSIMETRY

BACKGROUND OF THE INVENTION

1. Field of Invention

The present invention relates to radiation film dosimetry, and more particularly to methods and devices for removing effects of variations in film processing and chemistry on radiation dose calibrations.

2. Discussion

An important use of radiotherapy is the destruction of tumor cells. In the case of ionizing radiation, tumor destruction depends on the "absorbed dose" or the amount of energy deposited within a tissue mass. Radiation physicists normally express the absorbed dose in cGy units or centigray. One cGy equals 0.01 J/kg.

Radiation dosimetry generally describes methods to measure or predict the absorbed dose in various tissues of a patient undergoing radiotherapy. Accuracy in predicting and measuring absorbed dose is key to effective treatment and prevention of complications due to over or under exposure to radiation. Although many methods exist for measuring and predicting absorbed dose, radiation film dosimetry is often used because of its excellent spatial resolution (better than 1 mm) and its ability to measure dose distribution. In addition, film dosimetry is an integrative technique—the measured dose distribution represents the accumulated dose in an irradiated medium—which is necessary for undertaking dosimetry of dynamic treatment methods such as dynamic wedges, arc, and rotation therapy.

Radiation film dosimetry depends on the phenomenon that photographic or radiographic film will darken when exposed to ionizing radiation. The degree of darkening depends on the amount of radiation absorbed by the energy sensitive layer on the film, and can be quantified in terms of the film's optical density. One may calculate the optical density, OD, from the expression:

$$OD = \log_{10}\left(\frac{\Phi_0}{\Phi}\right), \quad \text{I}$$

where $\Phi_0$ and $\Phi$ represent, respectively, the intensity of light (photons) striking and passing through the film. Note, however, that all of the methods disclosed below use the term optical density more generally to describe any quantity that provides a measure of film opacity.

In typical film dosimetry, a technician makes one or more calibration films by irradiating unique areas of the films with different radiation dose levels (cGy) using a linear accelerator. Next, the technician develops the calibration films and scans them with a film digitizer, which converts each of the films to an array of pixels having values representing the optical density at each point on a particular calibration film. Knowing the radiation dose levels of the exposed areas of the films, a radiation physicist, usually with the aid of specialized computer software, develops a calibration or H&D curve, which relates film optical density to radiation dose.

Armed with the H&D curve, the radiation physicist can quantify beam characteristics of the linear accelerator through subsequent exposure, development, and OD measurements of radiographic films. For example, as part of a treatment plan or quality assurance procedure, the radiation physicist can use film dosimetry to generate depth dose profiles, isodose and isodensity contours, and cross section profiles. In addition, the physicist can use film dosimetry to perform flatness and symmetry analyses, and to carry out field width calculations, among others. Usually, the physicist uses computer software that automatically calculates and displays beam characteristics from scanned and digitized radiographic films. Useful software for generating the H&D curve and for analyzing radiotherapy beam characteristics includes RIT113 FILM DOSIMETRY SYSTEM, which is available from Radiological Imaging Technology.

Film dosimetry offers many advantages over competing methods, but its use is often limited by its variability—a film exposed to the same dose of ionizing radiation as an earlier film may exhibit a significantly different optical density. Much of the variability in film dosimetry can be traced to film processing. For example, in a commercial film processor a temperature change as small as one degree Celsius can cause significant changes in optical density. Other film processing variables, such as the age and strength of chemicals in the film processor, and the number and type of films processed can contribute to changes in optical density. In addition, it is known that films from two different manufacturing lots can exhibit significantly different optical density following exposure to the same dose of radiation.

Three methods have been used to circumvent film-processing variations, but each suffers serious drawbacks. In the first method, a fresh set of calibration films are exposed and developed along with each group of test films that are associated with a separate treatment plan or QA procedure. Thus, for each set of test films, the first method requires that a technician expose an additional ten to twenty five calibration films, which improves the accuracy of film dosimetry but consumes considerable resources. In the second method, the dose at any point on a given film image is expressed as a percentage or fraction of the maximum dose or optical density of the film image. Although the second method, which is known as "relative dosimetry," can correct gross variations in film processing, it is only useful in applications that do not require an absolute measurement of dose.

The third method is similar to the first method, but relies on the observation that despite differences in film processing conditions and film chemistry, most H&D curves exhibit similar shape. Like the first method, a set of calibration films are exposed and developed along with each group of test films. But instead of exposing a full set of calibration films, the technician exposes only two films, which bracket the dose range of the test films. The two films—a low optical density film and a high optical density film—represent "endpoints" of the H&D curve. Since most H&D curves have similar shape, one uses the two endpoints to adjust the original H&D curve. In other words, the method approximates the original H&D curve with a mathematical function, and uses the endpoints to adjust the original H&D curve fit. Although the third method appears promising, the radiation therapy community has failed to adopt it. Recent analyses indicate that "end point" calibration corrections may lead to significant error because film-processing variations and film chemistry differences can affect the central region of the H&D curve more than the endpoints. In addition, the method appears strongly dependent on exposure (operator) technique.

The present invention endeavors to overcome, or at least minimize, one or more of the problems described above.

SUMMARY OF THE INVENTION

The present invention provides a fast and accurate method of correcting errors in film dosimetry measurements arising from temporal changes in radiographic film processing and manufacturing. The method includes irradiating separate and distinct areas of one or more calibration films with different radiation dose levels to obtain a first calibration that comprises data pairs of optical density (or a quantity related to optical density, such as light intensity) and radiation dose. The method also includes exposing a non-irradiated portion of at least one (and typically all) of the calibration films to light from an array of standardized light sources to obtain a first optical density step gradient. During preparation of test films, which are part of a QA procedure or patient treatment plan, the method provides for exposing a non-irradiated portion of the test film (or films) to light from the array of standardized light sources to obtain a second optical density step gradient. Since the characteristics of each of the standardized light sources change little from one exposure to the next, any deviations in the optical density step gradient among different films result, presumably, from changes in film processing or differences in film chemistry. Hence, the method includes modifying either the first calibration or the optical density values of the test films based on differences between the first and second optical density step gradients.

Unlike conventional methods, the present invention provides an accurate correction over the full range of optical densities encountered in film dosimetry. In addition, use of the inventive method should result in considerable cost savings since it substantially reduces the number of calibration films that must be prepared in conventional film dosimetry. Moreover, for about the same expenditure of time and labor associated with relative film dosimetry, the present invention yields absolute measurements of absorbed dose.

DETAILED DESCRIPTION OF THE PREFERRED EMBODIMENTS

Figure 1:
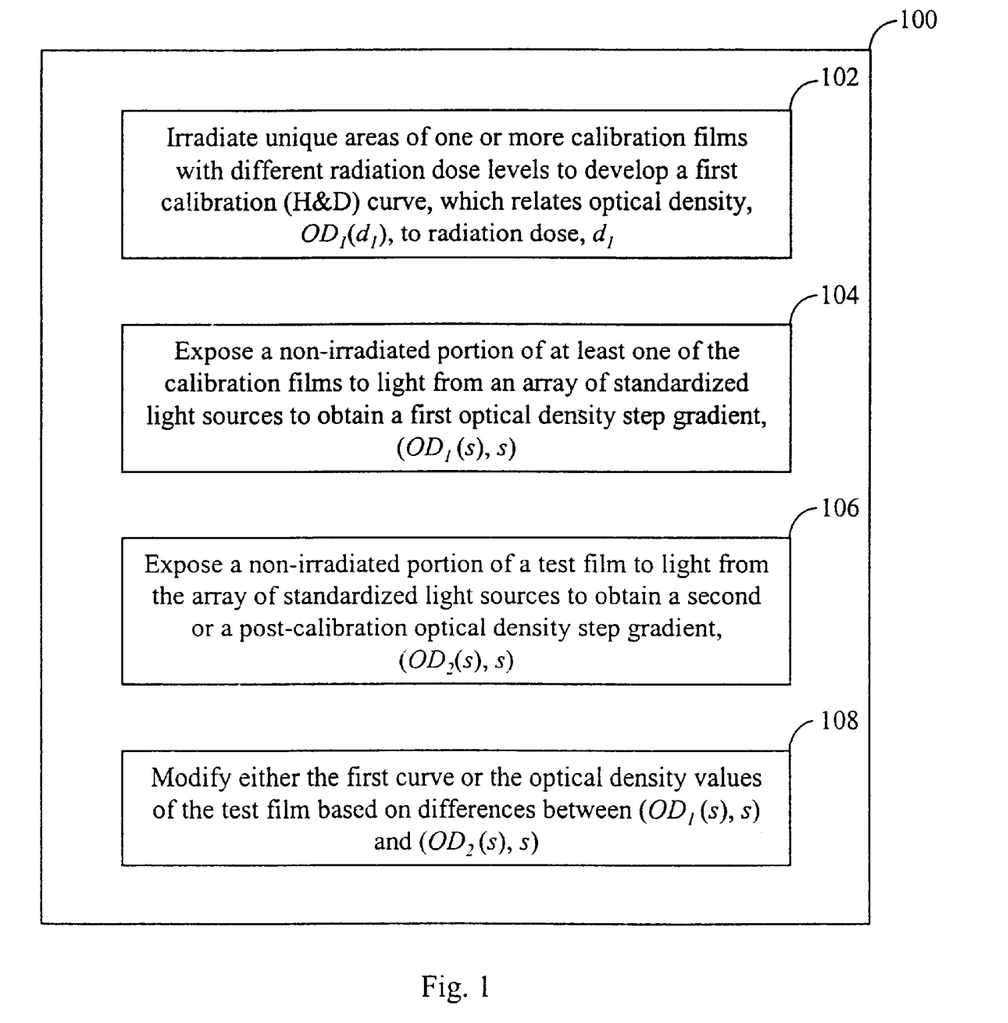
FIG. 1 shows a process flow diagram of a method for adjusting a film dosimetry calibration in response to changes in film processing conditions and chemistry.

FIG. 1 illustrates a method 100 for use in film dosimetry that removes or diminishes effects of variations in film processing and chemistry on radiation dose calibrations. As in conventional film dosimetry, the method 100 includes irradiating 102 unique areas of one or more calibration films with different radiation dose levels (cGy) using a linear accelerator or other source of ionizing radiation. The number of dose levels can vary among applications and treatment centers, but typical calibration films comprise about ten to twenty five different dose levels. In addition, the radiation exposure range of the calibration films should encompass radiation dose levels of any subsequent treatment plan or quality assurance procedure. Following processing, one uses the irradiated calibration films to develop a first calibration or H&D curve, which relates optical density, $OD_1(d_1)$, to radiation dose, $d_1$.

As shown in FIG. 1, the method 100 also includes exposing 104 a non-irradiated portion of at least one (and typically all) of the calibration films to light from an array of standardized light sources prior to developing or processing the calibration films. Each of the standardized light sources delivers a fixed and reproducible amount of light to a spatially distinct area of the film. Once processed, the calibration films thus include separate darkened areas that correspond to irradiation at different dose levels and to exposure to individual lights of the array. Ordinarily, a technician scans the processed calibration films with a film digitizer, which converts each of the films to an array of pixels having values representing the optical density at each point or location on a particular calibration film. Knowing the radiation dose levels of the irradiated areas of the films, a radiation physicist, usually with the aid of specialized computer software, develops a calibration or an H&D curve, which relates film optical density to radiation dose. Similarly, the radiation physicist obtains a first optical density step gradient comprised of a set of ordered data pairs $(OD_1(s), s)$, where "s" refers to a particular standardized light source or "step."

Since intensity, exposure duration, wavelength and any other relevant characteristics of each of the standardized light sources varies little from one exposure 104 to the next, any deviations in the optical density step gradient among films results, presumably, from changes in film processing or differences in film chemistry. Thus, the method 100 includes exposing 106 a non-irradiated portion of a test film that is part of a subsequent treatment plan or QA procedure to light from the array of standardized light sources. Once processed, a technician scans the test film (or films) with a film digitizer to obtain a radiographic image of interest, $OD(x,y)$, and a second or a post-calibration optical density step gradient, $(OD_2(s_2), s)$. After obtaining $OD(x,y)$ and $(OD_2(s_2), s)$, the method 100 includes modifying 108 either the first calibration (H&D) curve or $OD(x,y)$ based on differences between the optical density step gradients, $(OD_1(s), s)$ and $(OD_2(s), s)$.

As discussed in the background of the invention, the method 100 uses the term optical density to denote any quantity that provides a measure of film darkness or opacity. For example, instead of using optical density as defined by equation I, the method 100 can use the intensity of light passing through the film, $\Phi$, or the fraction of light that reflects off the film, or the percent transmission of light passing through the film. Note, however, if the method 100 uses a quantity other than optical density as defined by equation I, then the same digitizer should be used when scanning films to ensure consistent measurement of film opacity.

Figure 2:
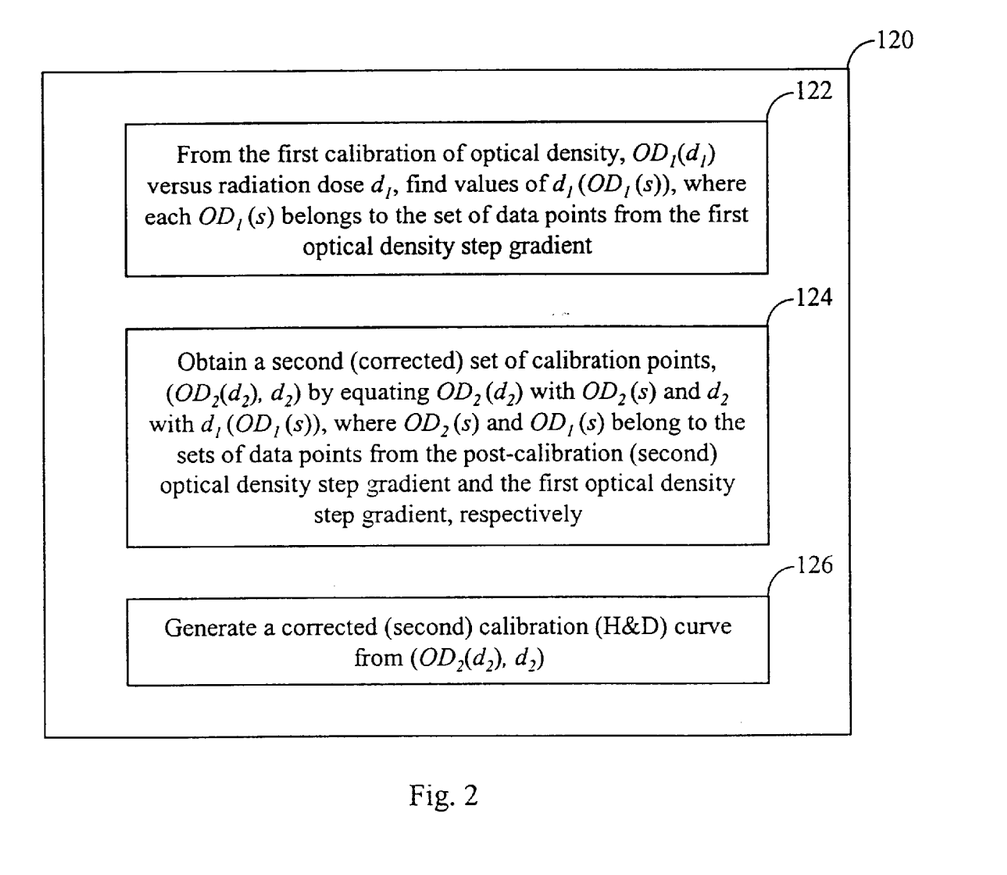
FIG. 2 shows a first method of modifying a calibration (H&D) curve.

FIG. 2 shows a method 120 of modifying the first calibration (H&D) curve—$OD_1(d_1)$ versus $d_1$—to account for any changes in film processing conditions, film manufacturing variations, and so on. The method 120 includes finding 122 dose values, $d_1(OD_1(s))$, that satisfy the first calibration curve and that correspond to optical density values equal to $OD_1(s)$. Each value of $OD_1(s)$ belongs to the set of data points, $(OD_1(s), s)$, which are obtained by exposing 104 calibration films to the array of standardized light sources (FIG. 1). Typically, the first calibration curve represents a function having a set of parameters that one adjusts to approximate or "fit" discrete data pairs of $OD_1(d_1)$ and $d_1$ in some best sense. The curve-fitting function is typically a linear or a nonlinear combination of simple functions such as polynomials or sines and cosines, and one determines values of the parameters by minimizing squares of differences between the function and the data points. Alternatively, the first calibration curve may represent one or more interpolating or extrapolating functions that satisfy each data pair exactly. Examples of interpolating and extrapolating functions include straight-line segments, cubic splines, rational functions, and Lagrange polynomials. Whether curve-fitting or interpolating (extrapolating), the method 120 typically provides the first calibration curve as a lookup table of equally spaced ordered pairs $(OD_1(d_1), d_1)$ or $(d_1(OD_1), OD_1)$ to minimize computation time. For a description of useful curve-fitting, interpolation, and extrapolation routines, including a discussion of searching a lookup table, see William H. Press et al., *Numerical Recipes in C*, 105–119, 656–706 (2d ed. 1992).

As shown in FIG. 2, after finding 122 $d_1(OD_1(s))$, the method 120 includes obtaining 124 a second (corrected) set of calibration points, $(OD_2(d_2), d_2)$, by equating $OD_2(d_2)$ with $OD_2(s)$ and $d_2$ with $d_1(OD_1(s))$, where $OD_2(s)$ and $OD_1(s)$ belong to sets of data points from the post-calibration (second) optical density step gradient and the first optical density step gradient, respectively. Finally, the method 120 includes generating 126 a second or corrected calibration (H&D) curve from the $(OD_2(d_2), d_2)$ pairs. Again, the second calibration curve may represent a function that "fits" discrete data pairs of $OD_2(d_2)$ and $d_2$ in some best sense, or may represent one or more interpolating or extrapolating functions that satisfy each data pair exactly. In any event, the second calibration curve is usually made available as a lookup table.

Figure 3:
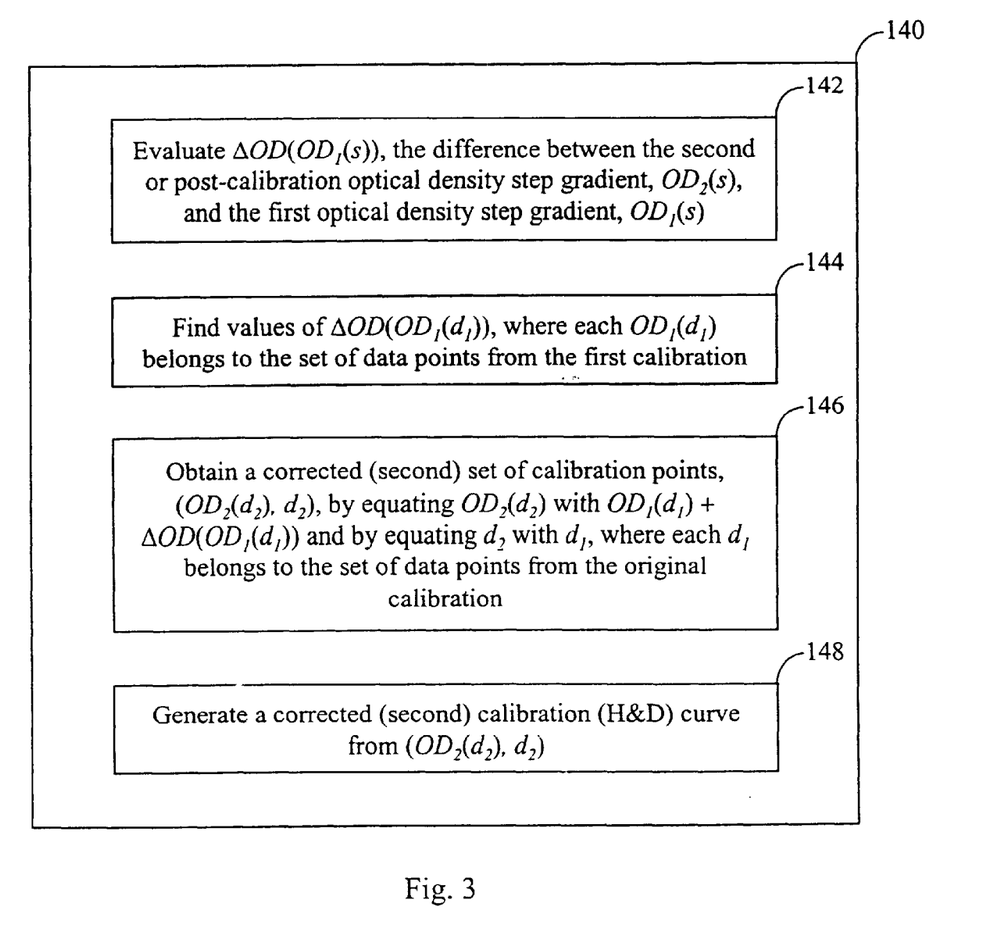
FIG. 3 shows a second method of modifying a calibration (H&D) curve.

FIG. 3 shows a second method 140 for correcting the first calibration (H&D) curve. The method 140 includes evaluating 142 a differences formula, $\Delta OD(OD_1(s))$, where $\Delta OD(OD_1(s))$ represents the difference between the second or post-calibration optical density step gradient, $OD_2(s)$, and the first optical density step gradient, $OD_1(s)$, for each step or standardized light source, s. By curve fitting or interpolating data pairs $(\Delta OD(OD_1(s)), OD_1(s))$, the method 140 includes finding 144 values of $\Delta OD(OD_1(d_1))$ that correspond to optical density values equal to $OD_1(d_1)$. Each value of $OD_1(d_1)$ belongs to the set of data points from the first calibration, which are obtained by irradiating 102 the calibration films with different radiation dose levels (FIG. 1). The method 140 also includes obtaining 146 a second (corrected) set of calibration points, $(OD_2(d_2), d_2)$ by equating $OD_2(d_2)$ with $OD_1(d_1)+\Delta OD(OD_1(d_1))$ and by equating $d_2$ with $d_1$, where each $d_1$ belongs to the set of data points from the first calibration. Finally, the method 140 includes generating 148 a corrected calibration (H&D) curve from $(OD_2(d_2), d_2)$ data pairs by curve-fitting or interpolating (extrapolating) as noted in the discussion of FIG. 2.

Figure 4:
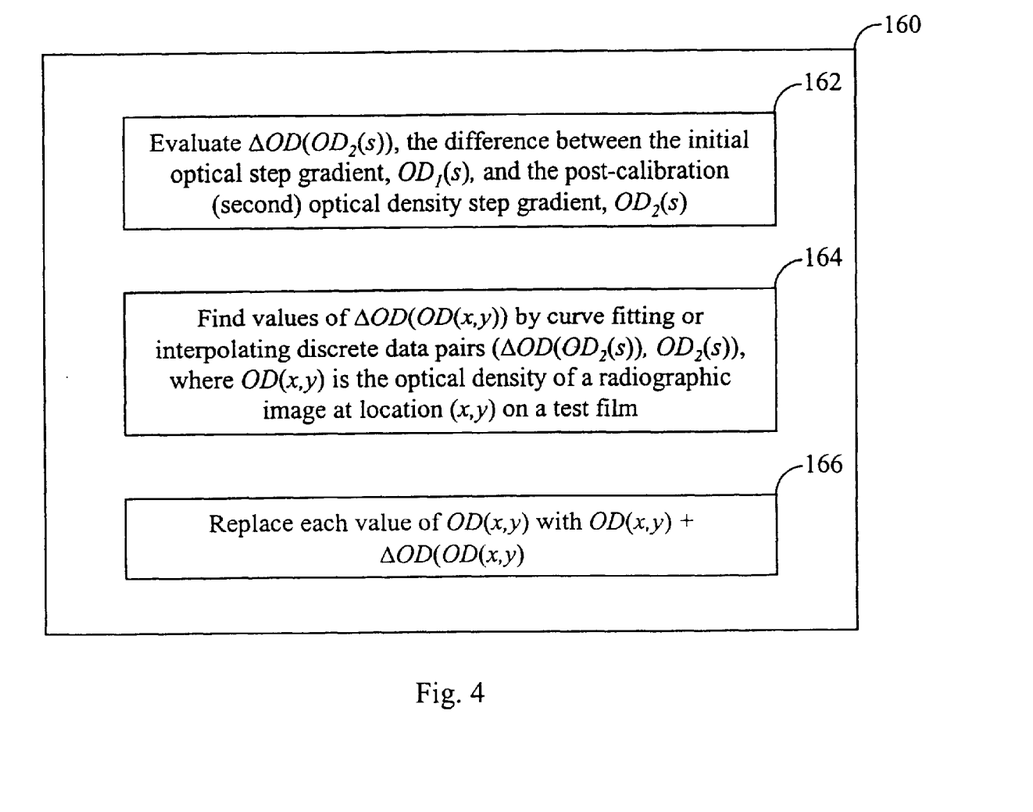
FIG. 4 shows a method of modifying individual optical density measurements of radiographic images on test films.

Instead of modifying the first calibration curve, one may alternatively modify individual optical density measurements of radiographic images on test films as shown in FIG. 4. The method 160 includes evaluating 162 a difference formula, $\Delta OD(OD_2(s))$, and by curve fitting or interpolating discrete data pairs $(\Delta OD(OD_2(s)), OD_2(s))$, finding 164 values of $\Delta OD(OD (x,y))$. Here, for each s, $\Delta OD(OD_2(s))$ represents the difference between the first optical step gradient, $OD_1(s)$, and the second or post-calibration optical density step gradient, $OD_2(s)$, and $OD(x,y)$ represents the optical density of a radiographic image at location $(x,y)$ on the test film. The method 160 adjusts the radiographic image by replacing 166 each $OD(x,y)$ with $OD(x,y)+\Delta OD(OD(x,y))$.

Figure 5:
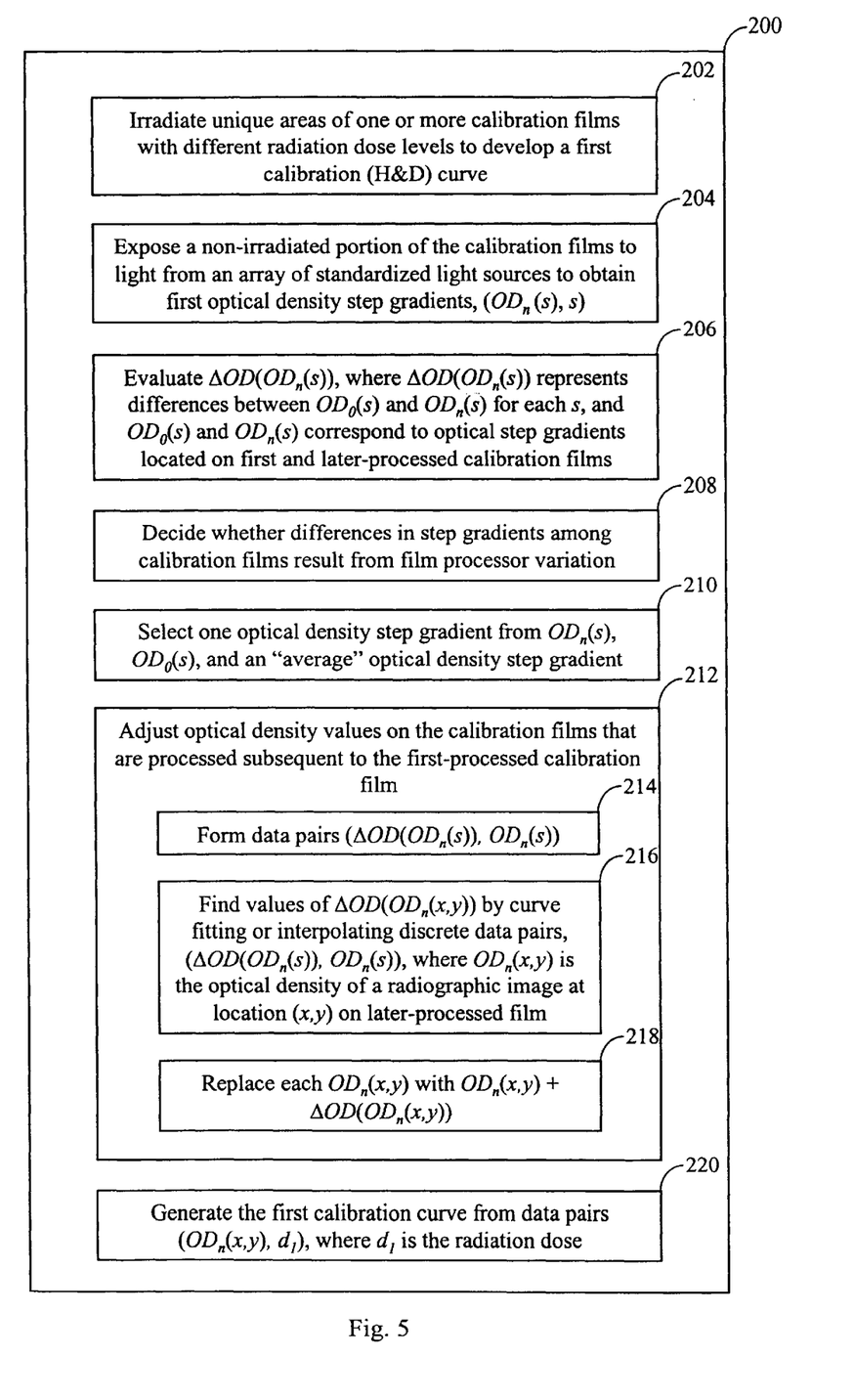
FIG. 5 shows a method of accounting for short-term film processor variation during the preparation of calibration films.

The method 100 shown in FIG. 1 will likely find greatest use in adjusting radiographic images made days, weeks or even months following the first calibration. However, one can use a similar method 200, which is shown in FIG. 5, to quantify short-term (hourly, for example) film processor variations during calibration film processing. The method 200 includes irradiating 202 unique areas of the calibration films with different radiation dose levels from a source of ionizing radiation, and exposing 204 a non-irradiated portion of some (typically all) of the calibration films to light from an array of standardized light sources prior to film processing. Since film processor conditions can vary during acquisition and development of multiple calibration films, the method 200 also includes evaluating 206 a difference formula, $\Delta OD(OD_n(s))$. Here, $\Delta OD(OD_n(s))$ represents, for each s, differences between $OD_0(s)$ and $OD_n(s)$, for each s, and $OD_0(s)$ and $OD_n(s)$ correspond to optical step gradients located on first and later-processed calibration films, respectively.

As shown in FIG. 5, the method 200 optionally includes deciding 208 whether any differences in the step gradients among calibration films are the result of unacceptable film processor variation. One useful technique for deciding 208 the source of the differences includes comparing a suitable metric, $\|OD\|$, to a user-supplied threshold value, $\rho$. If $\|OD\|$ exceeds $\rho$, for example, then the method 200 attributes the differences among optical density step gradients to film processor variations. Many metrics are available for characterizing differences in optical density step gradient. One useful metric is:

$$\|OD\|_a = \sqrt{\Sigma_{n=1}^N \Sigma_{s=1}^S (\Delta OD(OD_{n(s)}))^2},\qquad \text{II}$$

where N represents the number of calibration films or optical density step gradients, and S represents the number of steps (standardized light sources) in each of the optical density step gradients. Another useful metric is:

$$\text{Max}\|OD\|_b = \sqrt{(\Delta OD(OD_{n(s)}))^2}.\qquad \text{III}$$

In equation III, $\text{Max}\|OD\|_b$ refers to the largest value of the expression for any allowable value of n and s.

Assuming that differences in the optical density step gradients are small—not the result of film processor variations—the method 200 provides for selecting 210 an optical density step gradient from among $OD_n(s)$, $OD_0(s)$, and an "average" optical density step gradient, $\overline{OD(s)}$. One may determine $\overline{OD(s)}$ several ways including averaging values of $OD_n(s)$ and $OD_0(s)$ for each s or fitting all $OD_n(s)$ and $OD_0(s)$ to a single curve using numerical methods described above (see FIG. 2 and accompanying text).

If, however, differences in the optical density step gradients are not small or are not measured, then the method 200 provides for adjusting 212 optical density values on the calibration films that are processed subsequent to the first-processed calibration film. The adjustment 212 technique is analogous to modifying 160 the optical density of radiographic images on test films made after the calibration films (See FIG. 4 and accompanying discussion). Thus, the adjustment 212 technique includes forming 214 data pairs $(\Delta OD(OD_n(s)), OD_n(s))$ and finding 216 values of $\Delta OD(OD_n(x,y))$, where $OD_n(x,y)$ is the optical density of a radiographic image at location $(x,y)$ on later-processed calibration film. The method 200 adjusts 212 the radiographic image by replacing 218 each $OD_n(x,y)$ with $OD_n(x,y)+\Delta OD(OD_n(x,y))$. One can find 216 $\Delta OD(OD_n(x,y))$ by curve fitting or interpolating (extrapolating) discrete data pairs, $(\Delta OD(OD_n(s)), OD_n(s))$.

Finally, the method 200 includes generating 220 a first calibration (H&D) curve from data pairs $(OD_n(x,y), d_1)$. Assuming the differences in optical density step gradients are the result of unacceptable film processor variations, the method 200 uses values of $OD_n(x,y)$ that have undergone adjustment 212; otherwise, the method 200 uses values of $OD_n(x,y)$ as originally measured. The resulting first calibration curve finds use in the methods 100, 120, 140, 160 depicted in FIG. 1–FIG. 4.

Figure 6:
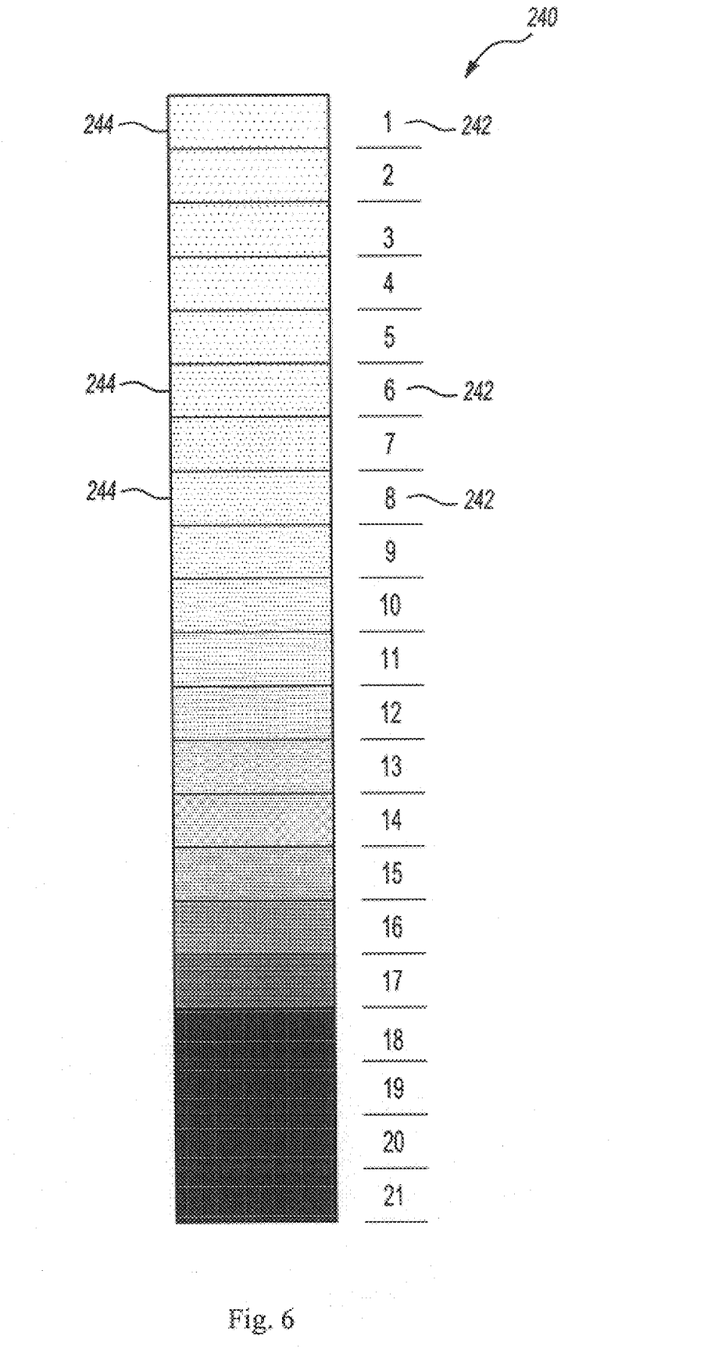
FIG. 6 shows a sensitometer strip, which can be used as an optical density step gradient.

In the methods 100, 200 shown in FIG. 1 and FIG. 5, useful standardized light arrays include sensitometers, which are widely used in diagnostic imaging. Sensitometers are available from a variety of vendors, including X-RITE, Inc, which markets Model 334, 383, 392 and 394 sensitometers. Each of these sensitometers generates an optical density step gradient in the form of a strip 240 as shown in FIG. 6. Each step number 242 refers to a specific area 244 of the film that has been exposed to one of the standardized light sources and thus corresponds to a different value of "s" in data pairs $(OD_1(s), s)$ or $(OD_2(s), s)$ of FIG. 1. Other commercial sensitometers may generate optical density step gradients in the form of wedges, circles, or other shapes.

Unlike the end-point calibration correction discussed in the background section, sensitometer output does not appear to depend on operator technique. To use a commercial sensitometer, the operator typically removes the radiographic film from its light-tight jacket in a darkroom, and clamps the sensitometer over an edge of the radiographic film. The operator presses a button on the sensitometer, which actuates each of the standardized light sources for a predetermined amount of time, exposing the edge of the film. Next, the operator unclamps the sensitometer and either immediately processes the film or returns the film to its light-tight jacket for later processing. Ordinarily, the operator repeats this process for each calibration or test film in a batch-wise process.

Figure 7:
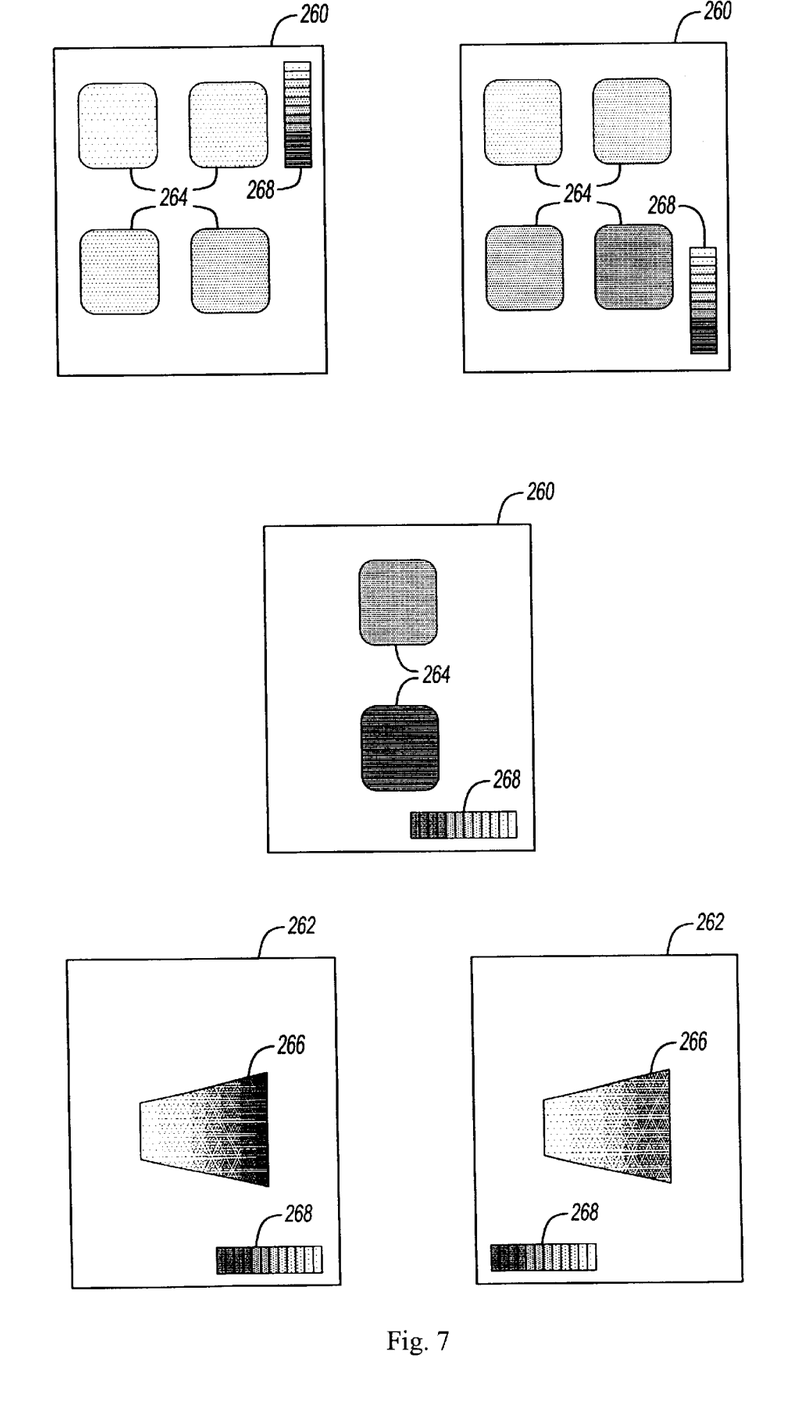
FIG. 7 shows calibration and test films prepared in accordance with the methods of FIG. 1 and FIG. 5.

FIG. 7 depicts calibration 260 and test 262 films prepared in accordance with the methods of FIG. 1 and FIG. 5. Each of the calibration 260 films have been exposed to different doses of ionizing radiation at unique areas resulting in dark or opaque regions 264 on the films 260. Similarly, each of the test films 262 have been exposed to ionizing radiation, say as part of a patient treatment plan or quality assurance procedure, resulting in opaque radiographic images 266. Furthermore, FIG. 7 shows that each of the calibration 260 and test 262 films have been exposed to light from an array of standardized light sources, such as a sensitometer, resulting in optical density step gradients 268 on each of the films 260, 262. As described above, differences in the optical density step gradients 268 allow correction of the calibration or optical density measurements.

The methods 100, 200 shown in FIG. 1 and FIG. 5, respectively, are robust and can be used with any radiographic film as long as the film will darken in response to ionizing radiation and light from the array of standardized light sources (a sensitometer, for example). In addition to changes in film processing conditions and lot-to-lot variations in radiographic film, the method 100 also may be able to account for differences among individual film processors. For example, the method 100 may be able to adjust the optical density-dose relationship of film processed with a first film processor to later films made with a second film processor.

As noted in the background of the invention, radiation physicists typically use computer software that automatically calculates and displays the H&D curve and beam characteristics from scanned and digitized radiographic films. Thus, portions of the methods shown in FIGS. 1–5 are typically implemented as software routines that run on a processor. Suitable processors include, for example, both general and special purpose microprocessors. Generally, a processor receives instructions and data from a read-only memory and/or a random access memory. Storage devices suitable for tangibly embodying computer program instructions and data include all forms of non-volatile memory, including, for example, semiconductor memory devices, such as EPROM, EEPROM, and flash memory devices; magnetic disks such as internal hard disks and removable disks; magneto-optical disks; and CD-ROM disks. One may supplement any of the foregoing by, or incorporate in, ASICs (application-specific integrated circuits).

To provide interaction with a user, one can implement portions of the methods 100, 200 on a computer system having devices for displaying information to the user and for allowing the user to input information to the computer system. Useful display devices include a monitor and LCD screen; suitable input devices include a keyboard, which can be used with a pointing device such as a pressure-sensitive stylus, a touch pad, a mouse or a trackball. In addition, the computer system may provide a graphical user interface through which the computer routines interact with the user.

The above description is intended to be illustrative and not restrictive. Many embodiments and many applications besides the examples provided would be apparent to those of skill in the art upon reading the above description. The scope of the invention should therefore be determined, not with reference to the above description, but should instead be determined with reference to the appended claims, along with the full scope of equivalents to which such claims are entitled. The disclosures of all articles and references, including patent applications and publications, are incorporated by reference for all purposes.

What is claimed is:

1. A method of reducing effects of film processing variations on radiation film dosimetry comprising:

irradiating unique areas of one or more calibration films with different radiation dose levels to obtain a first calibration relating optical density to radiation dose, the first calibration comprising data pairs of optical density, $OD_1(d_1)$, and radiation dose, $d_1$;

exposing a non-irradiated portion of at least one of the calibration films to light from an array of standardized light sources to obtain a first optical density step gradient, $(OD_1(s), s)$, wherein s refers to a particular standardized light source, exposing a non-irradiated portion of a test film to light from the array of standardized light sources to obtain a second optical density step gradient, $(OD_2(s), s)$; and modifying the first calibration based on differences between $(OD_1(s), s)$ and $(OD_2(s), s)$.

2. The method of claim 1, wherein modifying the first calibration comprises:

finding dose values, $d_1(OD_1(s))$, that satisfy the first calibration; and obtaining a second set of calibration points, $(OD_2(d_2), d_2)$, by equating $OD_2(d_2)$ with $OD_2(s)$ and $d_2$ with $d_1(OD_1(s))$.

3. The method of claim 1, wherein modifying the first calibration comprises:

evaluating a difference formula, $\Delta OD(OD_1(s))$, which represents differences between $OD_2(s)$ and $OD_1(s)$;

finding values of the difference formula, $\Delta OD(OD_1(d_1))$, wherein each $OD_1(d_1)$ satisfies the first calibration;

obtaining a second calibration, $(OD_2(d_2), d_2)$, by equating $OD_2(d_2)$ with $OD_1(d_1)+\Delta OD(OD_1(d_1))$ and by equating $d_2$ with $d_1$.

4. The method of claim 1, wherein the first calibration is obtained by irradiating more than one calibration film.

5. The method of claim 1, further comprising:

determining whether differences in optical density step gradients among calibration films result are the result of film processor variations using a suitable metric.

6. The method of claim 1, further comprising:

selecting the first optical density step gradient, $(OD_1(s), s)$, from among $OD_n(s)$, $OD_0(s)$, and an average optical density step gradient, wherein $OD_0(s)$ and $OD_n(s)$ correspond to optical step gradients located on first and later-processed calibration films, respectively.

7. The method of claim 4, further comprising:

adjusting optical density values of radiographic images on calibration films that are processed subsequent to a first-processed calibration film.

8. The method of claim 7, further comprising:

evaluating a difference formula, $\Delta OD(OD_n(s))$, wherein $\Delta OD(OD_n(s))$ represents, respectively, differences between an optical step gradient located on the first-processed calibration film and optical step gradients located on subsequent-processed calibration films, and subscript n denotes a particular calibration film;

finding values of the difference formula, $\Delta OD(OD_n(x,y))$, wherein $OD_n(x,y)$ represents the optical density at location $(x,y)$ on the calibration film denoted by subscript n; and replacing $OD_n(x,y)$ with $OD_n(x,y)+\Delta OD(OD_n(x,y))$.

9. A device for performing radiation film dosimetry calibrations, the device comprising a software routine tangibly embodied on a computer-readable medium and configured to modify a first calibration based on differences between first and second optical density step gradients, the first calibration comprising data pairs of optical density and radiation dose obtained by irradiating unique areas of one or more calibration films with different radiation dose levels, wherein the first optical step gradient is obtained by exposing a non-irradiated portion of at least one of the calibration films to light from an array of standardized light sources and the second step gradient is obtained by exposing a non-irradiated portion of a test film to light from the array of standardized light sources.

10. A system for performing radiation dosimetry calibrations, the system comprising a computer having a graphical user interface enabling a user to interact with a software routine running on the computer, the software routine configured to modify a first calibration based on differences between first and second optical density step gradients, the first calibration comprising data pairs of optical density and radiation dose obtained by irradiating unique areas of one or more calibration films with different radiation dose levels, wherein the first optical step gradient is obtained by exposing a non-irradiated portion of at least one of the calibration films to light from an array of standardized light sources and the second step gradient is obtained by exposing a non-irradiated portion of a test film to light from the array of standardized light sources.

11. The system of claim 10, further comprising an array of standardized light sources.

12. The system of claim 11, wherein the array of standardized light sources is a sensitometer.

13. A method of reducing effects of film processing variations on radiation film dosimetry comprising:

irradiating unique areas of one or more calibration films with different radiation dose levels to obtain a first calibration relating optical density to radiation dose, the first calibration comprising data pairs of optical density, $OD_1(d_1)$, and radiation dose, $d_1$;

exposing a non-irradiated portion of at least one of the calibration films to light from an array of standardized light sources to obtain a first optical density step gradient, $(OD_1(s), s)$, wherein s refers to a particular standardized light source;

exposing a non-irradiated portion of a test film to light from the array of standardized light sources to obtain a second optical density step gradient, $(OD_2(s), s)$;

modifying the optical density values of the test film based on differences between $(OD_1(s), s)$ and $(OD_2(s), s)$; and obtaining radiation dose using the first calibration and the modified optical density values of the test film.

14. The method of claim 13, wherein modifying the optical density values of the test film comprises:

evaluating a difference formula, $\Delta OD(OD_2(s))$, which represents differences between $OD_1(s)$ and $OD_2(s)$;

finding values of the difference formula, $\Delta OD(OD(x,y))$, wherein $OD(x,y)$ is the optical density of a radiographic image at location $(x,y)$ on a test film; and replacing values of $OD(x,y)$ with $OD(x,y)) \Delta OD(OD(x,y)$.

* * * * *